US011653865B2

(12) United States Patent
Lee et al.

(10) Patent No.: US 11,653,865 B2
(45) Date of Patent: May 23, 2023

(54) DEVICE FOR DETERMINING REMOVABILITY OF FOLEY CATHETER

(71) Applicants: INDUSTRY-ACADEMIC COOPERATION FOUNDATION, YONSEI UNIVERSITY, Seoul (KR); SEOUL NATIONAL UNIVERSITY R&DB FOUNDATION, Seoul (KR)

(72) Inventors: Kwang Suk Lee, Seoul (KR); Hyung Min Park, Seoul (KR); Dae Hyun Choi, Seoul (KR)

(73) Assignees: INDUSTRY-ACADEMIC COOPERATION FOUNDATION, YONSEI UNIVERSITY, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 17/856,640

(22) Filed: Jul. 1, 2022

(65) Prior Publication Data

US 2022/0330865 A1 Oct. 20, 2022

Related U.S. Application Data

(63) Continuation of application No. PCT/KR2020/018848, filed on Dec. 22, 2020.

(30) Foreign Application Priority Data

Jan. 2, 2020 (KR) ........................ 10-2020-0000288

(51) Int. Cl.
*A61B 5/20* (2006.01)
*A61M 25/00* (2006.01)
*A61B 5/00* (2006.01)

(52) U.S. Cl.
CPC .............. *A61B 5/205* (2013.01); *A61B 5/207* (2013.01); *A61B 5/6852* (2013.01); *A61B 5/742* (2013.01);
(Continued)

(58) Field of Classification Search
CPC ...... A61M 25/0662; A61M 2025/0001; A61M 2210/1085; A61M 25/0017;
(Continued)

(56) References Cited

U.S. PATENT DOCUMENTS

| 2008/0103408 | A1 | 5/2008 | Denton et al. |
| 2015/0230745 | A1* | 8/2015 | Wang ..................... A61B 5/205 600/561 |
| 2020/0390381 | A1* | 12/2020 | Cooper .................. A61B 5/205 |

FOREIGN PATENT DOCUMENTS

| JP | 2015159884 A | 9/2015 |
| JP | 2016123434 A | 7/2016 |

(Continued)

OTHER PUBLICATIONS

Notice of Patent Grant issued in corresponding KR Application No. 10-2020-0000288, dated Jul. 2, 2022, English Translation, 4 pages.
(Continued)

*Primary Examiner* — David J. McCrosky
(74) *Attorney, Agent, or Firm* — Burris Law, PLLC

(57) ABSTRACT

A device can be coupled to a foley catheter inserted into the bladder of a patient, where the foley catheter includes a urine passage through which urine can be drained from the bladder. The device includes a pressure sensor that is connected to a urine outlet of the urine passage and configured to measure a pressure value of the urine being drained through the urine outlet, a processor connected to the pressure sensor and configured to determine whether the foley catheter can be removed by comparing the pressure
(Continued)

value and a predetermined threshold value, and a display unit connected to the processor and displaying whether the foley catheter can be removed according to the control of the processor.

6 Claims, 5 Drawing Sheets

(52) U.S. Cl.
CPC .... *A61M 25/0017* (2013.01); *A61M 25/0075* (2013.01); *A61B 2562/0247* (2013.01); *A61M 2025/0001* (2013.01); *A61M 2025/0002* (2013.01); *A61M 2025/0076* (2013.01); *A61M 2205/502* (2013.01); *A61M 2205/584* (2013.01); *A61M 2205/587* (2013.01); *A61M 2210/1085* (2013.01)

(58) Field of Classification Search
CPC .. A61M 2205/502; A61B 5/205; A61B 5/202; A61B 5/204; A61B 5/208; A61B 5/20; A61B 5/207; A61B 5/201; A61B 2562/0247; A61B 5/742
See application file for complete search history.

(56) References Cited

FOREIGN PATENT DOCUMENTS

| KR | 20130115844 A | 10/2013 |
| KR | 1020130115844 A | 10/2013 |
| KR | 1020140087642 A | 7/2014 |
| KR | 1020150096202 A | 8/2015 |
| KR | 10188107 B1 | 8/2018 |
| KR | 101888107 B1 | 8/2018 |

OTHER PUBLICATIONS

International Search Report and Written Opinion, issued in corresponding International Application No. PCT/KR2020/018848, dated Jun. 9, 2021, 11 pages.
Office Action issued in corresponding KR Application No. 10-2020-0000288, dated Aug. 6, 2021, and an English translation thereof, 12 pages.

* cited by examiner

DEVICE FOR DETERMINING REMOVABILITY OF FOLEY CATHETER

CROSS-REFERENCE TO RELATED APPLICATION

This application is a continuation of International Application No. PCT/KR2020/018848, filed on Dec. 22, 2020, which claims priority to and the benefit of Korean Application No. 10-2020-0000288, filed on Jan. 2, 2020. The disclosures of the above applications are incorporated herein by reference.

FIELD

The present disclosure relates to a device for determining whether to remove a Foley catheter. Specifically, the present disclosure relates to a device for determining whether to remove a Foley catheter from the bladder of a patient, into which the Foley catheter is inserted, due to a urination disorder or the like.

BACKGROUND

The statements in this section merely provide background information related to the present disclosure and may not constitute prior art.

A Foley catheter is a tube through which urine flows or is discharged from a bladder of a patient having a urination disorder to an external urine bag. The Foley catheter is inserted into the bladder of the patient through the urethra.

The Foley catheter is used when the patient has a urination disorder and thus cannot urinate by himself/herself, or when a surgeon fills the bladder of the patient with saline or the like or performs urethral surgery. Excessive accumulation of the urine in the bladder of the patient having a urination disorder may cause pain to the kidneys, injury to the bladder, reflux of the urine, or the like. Insertion of the Foley catheter into the bladder of the patient may allow the urine to be discharged from the bladder of the patient who cannot urinate by himself/herself.

The insertion of the Foley catheter causes severe pain to the patient. Further, from the viewpoint of the medical staff, whether the patient is discharged may be determined only when the Foley catheter has been removed. Thus, both the patient and the medical staff generally want to remove the Foley catheter as soon as possible.

The removal of the Foley catheter is related to whether the patient urinates by himself/herself. In a general case, whether to remove the Foley catheter is determined through a Foley training method. In detail, whether to remove the Foley catheter is determined by whether the patient experiences an urge to urinate in a state in which the Foley catheter is locked. However, even when the patient has the urge to urinate and when the patient cannot urinate by himself/herself after the Foley catheter is removed, the Foley catheter should be inserted into the bladder of the patient again.

Since the Foley training relies on subjective judgment of the patient without objective numerical values, the patient from which the Foley catheter is removed because the patient is determined to be able to urinate by himself/herself on the basis of the urge to urinate may not actually discharge the urine by himself/herself. When the Foley catheter is inserted into such a patient again, severe pain occurs, and the discharge of the patient is delayed.

Thus, a device for determining whether to remove the Foley catheter on the basis of not the subjective judgment of the patient but the objective numerical values is required.

Further, a device which can quickly and simply determine and display whether to remove the Foley catheter inserted into the bladder of the patient on the basis of a measured value is required.

In a urodynamic test, the form of urine of a patient who urinates is measured. However, the determination of whether to remove the Foley catheter is based on the measurement of a urine-based numerical value for a patient in which the possibility of discharging urine is unclear. Thus, a device that may fill, with a fluid in a short time, the bladder of a patient, in which the possibility of discharging urine is unclear, and also measure a numerical value for the urine discharged from the bladder of the patient in order to shorten a time required to measure the numerical value is required.

There are various types of the Foley catheter such as a one-way Foley catheter including only a urine passage, a two-way Foley catheter including a passage for inflating a balloon and a urine passage, a three-way Foley catheter including a passage for inflating a balloon, a urine passage, and a passage through which a fluid passes, and the like. Thus, a device that may be commonly applied regardless of the type of the Foley catheter and determine whether to remove the Foley catheter is required.

SUMMARY

This section provides a general summary of the disclosure and is not a comprehensive disclosure of its full scope or all of its features. The present disclosure is directed to providing a device capable of determining whether to remove a Foley catheter on the basis of an objective value by measuring a pressure of urine discharged through the Foley catheter already inserted into the bladder of a patient.

The present disclosure is directed to also providing a device capable of immediately, quickly, and simply determining and displaying whether to remove a Foley catheter using the Foley catheter already inserted into the bladder of the patient.

The present disclosure is directed to also providing a device capable of filling, with a fluid in a short time, the bladder of the patient in which whether the discharge of urine is possible is unclear, and furthermore, measuring a numerical value for the urine discharged from the bladder of the patient.

The present disclosure is directed to also providing a device capable of being commonly applied regardless of the type of the Foley catheter and determining whether to remove the Foley catheter.

One aspect of the present disclosure provides a device to be coupled to a Foley catheter already inserted into a bladder of a patient, the Foley catheter including a urine passage through which urine is discharged from the bladder, and the device includes a pressure sensor connected to a urine outlet of the urine passage and configured to measure a pressure value of the urine discharged through the urine outlet, a processor connected to the pressure sensor and configured to determine whether to remove the Foley catheter by comparing the pressure value with a predetermined threshold value, and a display unit connected to the processor and configured to display whether to remove the Foley catheter under control of the processor.

The present disclosure provides a device which can determine whether to remove a Foley catheter on the basis of an objective value by measuring a pressure of urine discharged through the Foley catheter already inserted into the bladder of a patient.

The present disclosure also provides a device which can immediately, quickly, and simply determine and display whether to remove a Foley catheter using the Foley catheter already inserted into the bladder of the patient.

The present disclosure also provides a device which can fill, with a fluid in a short time, the bladder of the patient, in which a possibility of discharging urine is unclear, and also measure a numerical value for the urine discharged from the bladder of the patient.

The present disclosure also provides a device which can be applied regardless of the type of the Foley catheter and determine whether to remove the Foley catheter.

The effects obtained in the present disclosure are not limited to the effects described above, and other effects not described will be clearly understood by those skilled in the art to which the present disclosure pertains from the following description.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

Terms used herein are merely used to describe specific embodiments and may not be intended to limit the scope of other embodiments. Singular expressions may include plural expressions unless clearly otherwise indicated in the context. Terms used herein including technical or scientific terms have the same meanings as those commonly understood by those skilled in the art disclosed in the present disclosure. Terms defined in a general dictionary among the terms used herein may be interpreted as the same or similar meanings as or to the meanings in the context of the related art and are not interpreted as ideal or excessively formal meanings unless explicitly defined in the present disclosure. In some cases, even terms defined in the present disclosure may not be interpreted to exclude embodiments of the present disclosure.

Figure 1:
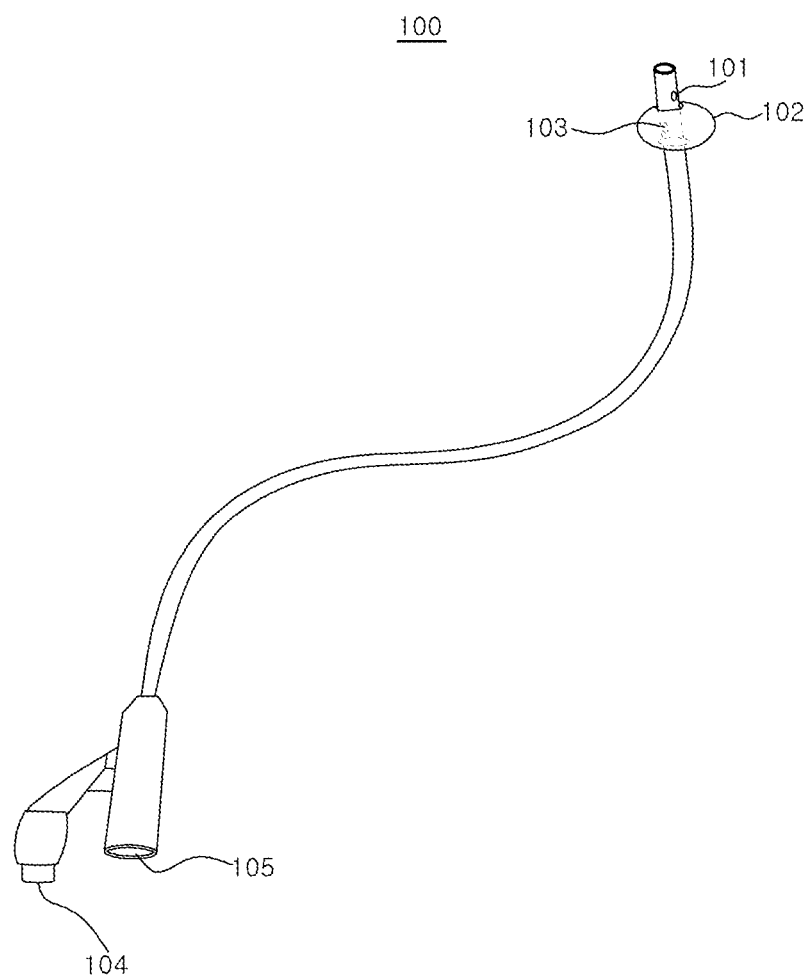
FIG. 1 illustrates an example of a configuration of a Foley catheter.

FIG. 1 illustrates an example of a configuration of a Foley catheter.

In detail, FIG. 1 illustrates a two-way Foley catheter having two ports at one end thereof.

Referring to FIG. 1, a urine inlet 101, a balloon 102, and a fluid outlet 103 formed at one end of the Foley catheter 100 are inserted into a bladder. The balloon 102 is inflated by a fluid introduced through the fluid inlet 104 and then discharged into the bladder through the fluid outlet 103. The fluid includes saline, air, or the like. The inflated balloon 102 maintains a position of the Foley catheter 100 within the bladder.

The other end of the Foley catheter 100 includes the fluid inlet 104 and a urine outlet 105. The fluid inlet 104 is used to inject the fluid for inflating the balloon 102. The urine outlet 105 is used to discharge the urine introduced from the bladder through the urine inlet 101. The urine outlet 105 may be connected to a urine bag.

According to various embodiments of the present disclosure, a urine passage through which the urine moves and a fluid passage through which the fluid moves may be formed inside the Foley catheter 100. Both ends of the urine passage correspond to the urine inlet 101 and the urine outlet 105, and both ends of the fluid passage correspond to the fluid inlet 104 and the urine outlet 105.

Figure 2:
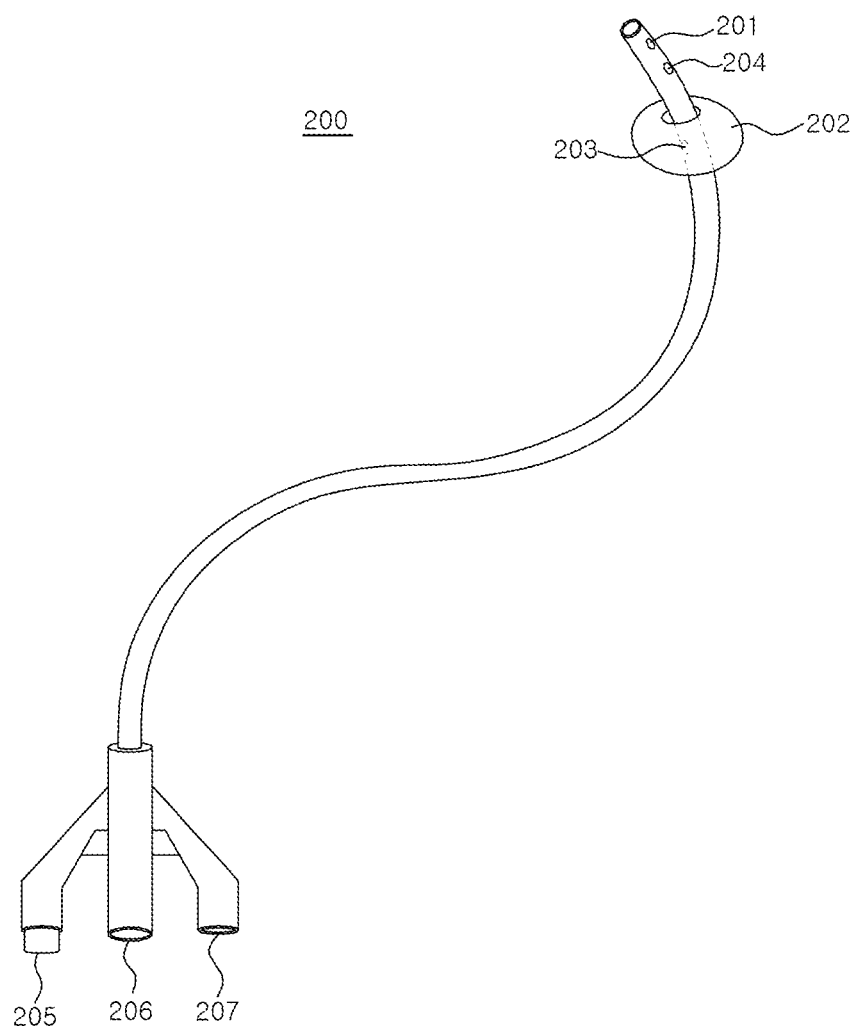
FIG. 2 illustrates an example of the configuration of the Foley catheter.

FIG. 2 illustrates an example of the configuration of the Foley catheter.

In detail, FIG. 2 illustrates a three-way Foley catheter having three ports at one end thereof.

Referring to FIG. 2, a urine inlet 201, a balloon 202, a first fluid outlet 203, and a second fluid outlet 204 formed at one end of a Foley catheter 200 are inserted into the bladder. The balloon 202 is inflated by a fluid introduced through a first fluid inlet 205 and then discharged into the bladder through the first fluid outlet 203. The fluid includes saline, air, or the like. The inflated balloon 202 maintains a position of the Foley catheter 200 within the bladder. Fluids such as drugs and saline introduced through a second fluid inlet 207 flows into the bladder through the second fluid outlet 204.

The other end of the Foley catheter includes the first fluid inlet 205, the second fluid inlet 207, and a urine outlet 206. The first fluid inlet 205 is used to inject the fluid for inflating the balloon 202. The second fluid inlet 207 is used to inject the fluid into the bladder. The urine outlet 206 is used to discharge the urine introduced from the bladder through the urine inlet 201. The urine outlet 206 may be connected to a urine bag.

According to various embodiments of the present disclosure, a urine passage through which the urine moves and first and second fluid passages through which the fluid moves may be formed inside the Foley catheter 200. Both ends of the urine passage correspond to the urine inlet 201 and the urine outlet 206, both ends of the first fluid passage correspond to the first fluid inlet 205 and the first fluid outlet 203, and both ends of the second fluid passage correspond to the second fluid inlet 207 and the second fluid outlet 204.

Referring to FIGS. 1 and 2, examples of the two-way Foley catheter and the three-way Foley catheter have been described, but the present disclosure is not limited thereto. For example, various embodiments of the present disclosure may be applied even to a one-way Foley catheter including only a urine passage without a balloon. Further, various embodiments of the present disclosure may be applied even to a Foley catheter additionally including another fluid inlet and another fluid passage compared to the Foley catheter of FIG. 1 or 2.

Figure 3:
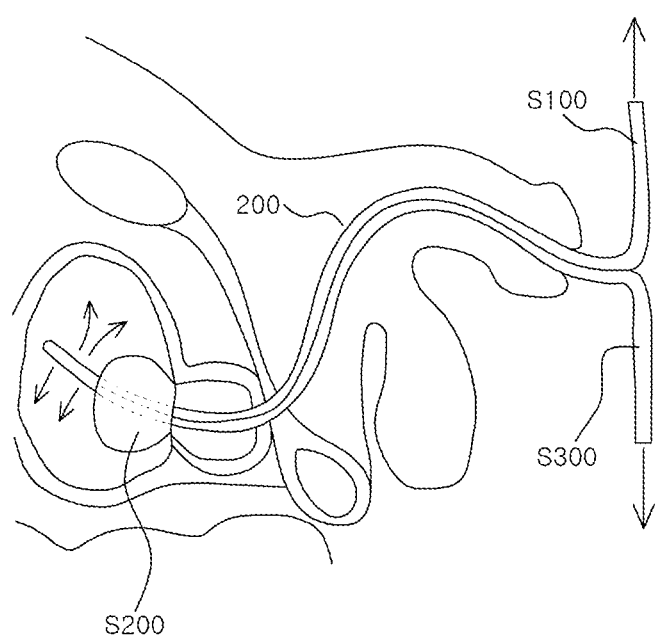
FIG. 3 illustrates an example of an operation process when the Foley catheter is inserted into the bladder of a patient.

FIG. 3 illustrates an example of an operation process when the Foley catheter is inserted into the bladder of a patient.

FIG. 3 illustrates a general operation process when the Foley catheter 200 of FIG. 2 is inserted into the bladder as an example of the Foley catheter.

In operation S100, the fluid is injected into the bladder through the second fluid inlet 207.

In operation S200, the balloon 202 in the bladder is inflated to maintain the position of the Foley catheter 200.

In operation S300, the urine introduced from the bladder is discharged through the urine outlet 206.

Figure 4:
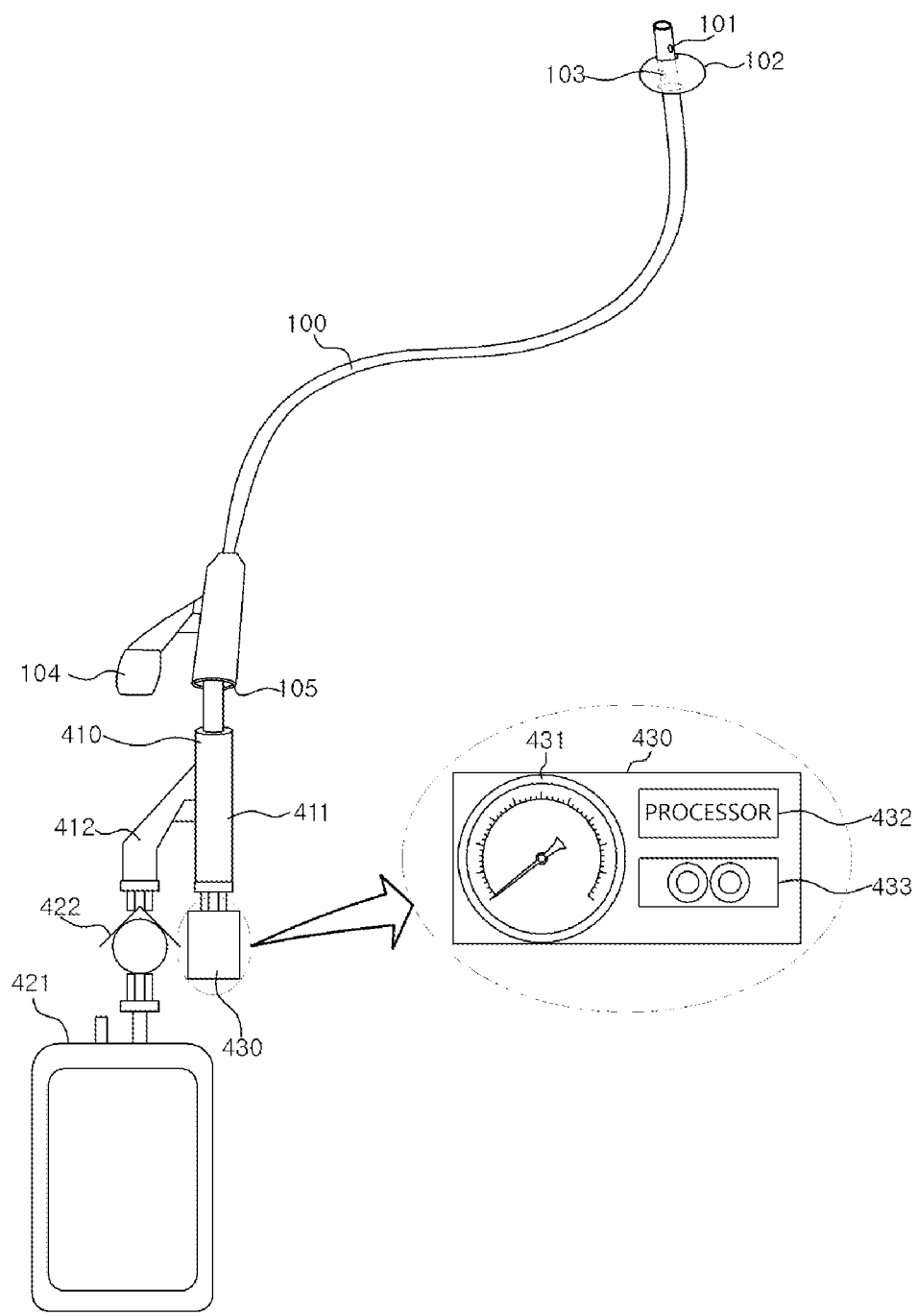
FIG. 4 illustrates a configuration of a device for determining whether to remove the Foley catheter according to various embodiments of the present disclosure.

FIG. 4 illustrates a configuration of a device for determining whether to remove the Foley catheter according to various embodiments of the present disclosure.

FIG. 4 illustrates a configuration in which the device for determining whether to remove the Foley catheter according to various embodiments of the present disclosure is mounted on the Foley catheter 100 of FIG. 1.

Whether the Foley catheter 100 is removed indicates whether the patient discharges the urine by himself/herself after the Foley catheter 100 is removed.

The device for determining whether to remove the Foley catheter, which is illustrated in FIG. 4, may be applied to a Foley catheter as long as the Foley catheter has a urine passage, even when the Foley catheter is not the two-way Foley catheter.

That is, the device for determining whether to remove the Foley catheter, which is illustrated in FIG. 4, may be applied to a Foley catheter as long as the Foley catheter has a urine passage.

Referring to FIG. 4, the device for determining whether to remove the Foley catheter includes a connection tube 410, a check valve 422, and a device unit 430. The device unit 430 includes a pressure sensor 431, a processor 432, and a display unit 433.

The urine outlet 105 is connected to the connection tube 410.

The connection tube 410 is configured in a form in which a passage connected from the urine outlet 105 branches off into two branches 411 and 412.

Among the two branches, the first branch 411 is connected to the pressure sensor 431, and the second branch 412 is configured to receive a fluid such as saline solution 421.

The first branch 411 may be disposed on an extension line with the urine outlet 105, and the second branch 412 may be disposed obliquely with respect to the extension line from the urine outlet 105. As a result, the urine discharged from the urine outlet 105 may directly flow to the first branch 411, and the amount of urine flowing to the second branch 412 can be minimized.

The check valve 422 may be disposed in the second branch 412.

The check valve 422 allows the fluid to flow in one direction. The check valve 422 is configured to allow the fluid, that is, saline or urine, passing through the second branch to flow only toward the urine outlet 105.

The check valve 422 prevents the urine discharged from the urine outlet 105 from flowing to the second branch. Even when the urine discharged from the urine outlet 105 flows from the second branch 412 to the check valve 422, the urine cannot pass through the check valve 422, and thus the urine has no choice but to flow toward the pressure sensor 431 of the device unit 430 through the first branch.

Due to the check valve 422, the fluid may be injected toward the bladder through the urine passage of the Foley catheter 100 in addition to the discharge of the urine that is an original purpose.

Since it is unclear whether the patient, in which the Foley catheter 100 is already inserted into the bladder, discharges urine by himself/herself, the patient is most likely not urinating when whether to remove the Foley catheter 100 is determined. Thus, in order to quickly determine whether to remove the Foley catheter 100, the urine may be discharged from the bladder of the patient only when the fluid such as saline should be injected into the bladder of the patient.

After a saline bag 421 having saline solution is connected to a branch on which the check valve 422 of the connection tube 410 is disposed. In following, the saline solution in the saline bag 421 may be provided as "saline solution 421." The saline solution 421 may be injected into the bladder through the urine passage through which the urine is not discharged. That is, the urine passage may be used not for the discharge of the urine that is the original purpose but as a passage for injection of the fluid while the patient having a urination disorder cannot discharge the urine.

After the saline solution 421 is sufficiently injected, when the urine starts to be discharged from the bladder through the Foley catheter 100, the urine passage is used as a passage for the discharge of the urine which is the original purpose.

The device for determining whether to remove the Foley catheter, which is described in FIG. 4, may use one urine passage due to the use of the check valve 422 to perform two tasks such as the injection of the saline solution 421 and the discharge of the urine.

There are various types of the Foley catheter such as a one-way Foley catheter including only a urine passage, a two-way Foley catheter including a passage for inflating a balloon and a urine passage, a three-way Foley catheter including a passage for inflating a balloon, a urine passage, and a passage through which a fluid passes, and the like. Thus, a device that may be applied regardless of the type of the Foley catheter and determine whether to remove the Foley catheter is required.

In the case of a patient having a general urination disorder, the two-way Foley catheter of FIG. 1 or the one-way Foley catheter having only the urine passage is inserted into the bladder due to costs or the like.

The device for determining whether to remove the Foley catheter, which is described in FIG. 4, may be applied regardless of the type of the Foley catheter because the two tasks such as the injection of the saline solution 421 and the discharge of the urine may be performed using the one urine passage due to the use of the check valve 422 when the urine passage is present in the Foley catheter.

The device unit 430 includes a pressure sensor 431, a processor 432, and a display unit 433.

The pressure sensor 431 is connected to the first branch 411 of the connection tube 410 and is configured to measure a pressure value of the urine discharged from the bladder of the patient through the urine outlet 105 and the first branch 411.

The processor 432 is connected to the pressure sensor 431. The processor 432 is configured to determine whether the Foley catheter may be removed by comparing the pressure value measured by the pressure sensor 431 with a predetermined threshold value.

The predetermined threshold value may be a pressure value measured through the pressure sensor 431 when the urine is normally discharged in a state in which the Foley catheter 100 of FIG. 4 is inserted into a normal person without a urination disorder in advance.

The predetermined threshold value may be set to a different value according to how a condition of the pressure value of the urine is set in determining whether to remove the Foley catheter.

According to an embodiment, when the pressure value is maintained at a value greater than the threshold value for a predetermined time, the processor 432 may be configured to determine that the Foley catheter 100 is to be removed. In this case, the threshold value may be set to a minimum pressure value measured for the predetermined time when the urine is normally discharged in a state in which the Foley catheter 100 and the device of FIG. 4 are inserted into the bladder of the normal person without a urination disorder. As the predetermined time becomes shorter, the threshold value may be set higher. For example, when the predetermined time is smaller than one second, the threshold value may be set to a peak value of the pressure value measured when the urine is normally discharged in a state in which the Foley catheter 100 and the device of FIG. 4 are inserted into the bladder of the normal person without a urination disorder.

According to an embodiment, the processor 432 may be further configured to determine a start time of the urine discharge as a time point at which the pressure value is greater than a predetermined specific value and determine an end time of the urine discharge as a time point at which the pressure value is smaller than the specific value. Here, the specific value is smaller than the threshold value. In this case, the predetermined specific value is zero or a value higher than zero and may be set as a pressure value measured when the urine starts to be discharged in a state in which the Foley catheter 100 and the device of FIG. 4 are inserted into the bladder of the normal person without a urination disorder.

According to an embodiment, the processor 432 may be further configured to determine that the Foley catheter 100 is to be removed when an average pressure value of the urine measured from the start time of the urine to the end time of the urine is greater than the threshold value. In this case, the threshold value may be set to a pressure value measured on average while the urine is discharged when the urine is normally discharged in a state in which the Foley catheter 100 and the device of FIG. 4 are inserted into the bladder of the normal person without a urination disorder.

According to an embodiment, the processor 432 is further configured to determine that the Foley catheter 100 is not to be removed when a peak value of the pressure value of the urine measured from the start time of the urine discharge to the end time of the urine discharge is smaller than the threshold value. In this case, the threshold value may be set to a peak value of the pressure value of the urine measured when the urine is normally discharged in a state in which the Foley catheter 100 and the device of FIG. 4 are inserted into the bladder of the normal person without a urination disorder.

According to an embodiment, the processor 432 may be further configured to determine that the Foley catheter 100 is not to be removed when an average pressure value of the urine measured from the start time of the urine discharge to the end time of the urine discharge is smaller than the threshold value. In this case, the threshold value may be set to a minimum pressure value measured for the predetermined time when the urine is normally discharged in a state in which the Foley catheter 100 and the device of FIG. 4 are inserted into the bladder of the normal person without a urination disorder. As the predetermined time becomes shorter, the threshold value may be set higher. For example, when the predetermined time is less than one second, the threshold value may be set to a peak value of the pressure value measured when the urine is normally discharged in a state in which the Foley catheter 100 and the device of FIG. 4 are inserted into the bladder of the normal person without a urination disorder.

The display unit 433 is connected to the processor 432 and displays whether to remove the Foley catheter 100 under the control of the processor 432.

According to an embodiment, the display unit 433 includes a light emitting diode of at least one color and may be configured so that a light emitting diode of a predetermined color corresponding to a removable state or a non-removable state of the Foley catheter 100 among light emitting diodes of at least one color may be configured to emit light under the control of the processor 432.

For example, a green light emitting diode is disposed to correspond to the removable state of the Foley catheter 100, and when the processor 432 determines the removable state of the Foley catheter 100 on the basis of comparison between the measured pressure value and the threshold value, the green light emitting diode may emit light under the control of the processor 432.

For example, a red-light emitting diode is disposed to correspond to the non-removable state of the Foley catheter 100, and when the processor 432 determines the non-removable state of the Foley catheter 100 on the basis of comparison between the measured pressure value and the threshold value, the red-light emitting diode may emit light under the control of the processor 432.

According to an embodiment, the display unit 433 includes a display capable of displaying a character or a figure and is configured to display a character or a figure meaning the removable state or the non-removable state of the Foley catheter 100 under the control of the processor 432.

Figure 5:
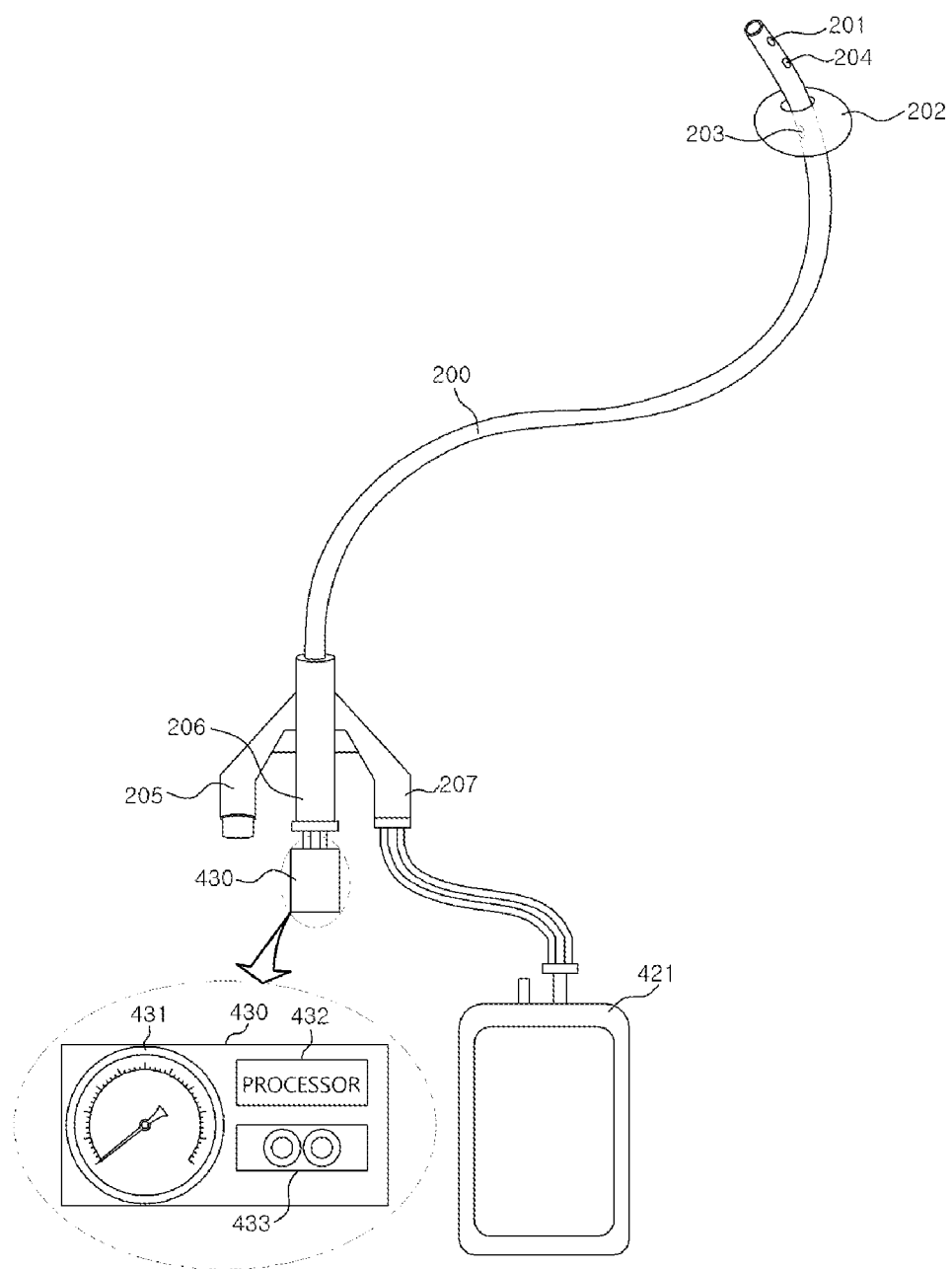
FIG. 5 illustrates a configuration of a device for determining whether to remove the Foley catheter according to various embodiments of the present disclosure.

FIG. 5 illustrates a configuration of a device for determining whether to remove the Foley catheter according to various embodiments of the present disclosure.

FIG. 5 illustrates a configuration in which a device for determining whether to remove the Foley catheter according to various embodiments of the present disclosure is mounted on the Foley catheter 200 of FIG. 2.

Whether to remove the Foley catheter 200 indicates whether the patient discharges the urine by himself/herself after the Foley catheter 200 is removed.

The device illustrated in FIG. 5 for determining whether to remove the Foley catheter may be applied to the three-way Foley catheter as illustrated in FIG. 5.

Referring to FIG. 5, the device for determining whether to remove the Foley catheter includes the device unit 430. The device unit 430 includes a pressure sensor 431, a processor 432, and a display unit 433.

The configuration of the device unit 430 is the same as that described in FIG. 4.

In the case of a device for the three-way Foley catheter as illustrated in FIG. 5, the saline solution may be injected into the bladder through the second fluid inlet 207 of the second fluid passage as a separate passage from the urine passage.

Further, after the saline solution 421 is injected through the second fluid inlet 207, even when the urine starts to be discharged from the bladder, the urine is discharged to the urine outlet 206 through the urine passage.

Thus, in the three-way Foley catheter 200 as illustrated in FIG. 5, there is no need to perform two tasks of injecting the saline solution 421 and discharging the urine using a single urine passage as illustrated in FIG. 4.

However, in the case of a patient having a general urination disorder, the two-way Foley catheter of FIG. 1 or the one-way Foley catheter having only the urine passage is inserted into the bladder due to costs or the like.

The device of FIG. 4 may be applied regardless of the type of the Foley catheter as long as there is a urine passage in the Foley catheter, but the device of FIG. 5 cannot be applied to the two-way Foley catheter.

Thus, as in the device of FIG. 5, as compared to the device of FIG. 4, a device without the connection tube 410 branching off into the two branches and the check valve 422 are less useful than the device of FIG. 4.

In the specific embodiments of the present disclosure described above, components included in the disclosure are expressed in singular or plural forms according to the presented specific embodiments. However, the singular or plural expression is selected suitable for a presented situation for convenience of description, the present disclosure is not limited to singular or plural components, the component may be configured in a singular form even when expressed in a plural form, and the components may be configured in a plural form even when expressed in the singular form.

Meanwhile, in a detailed description of the present disclosure, detailed embodiments have been described, but various modifications may be made without departing from the scope of the present disclosure. Therefore, the scope of the present disclosure is not limited to the described embodiments and may be defined by equivalents of the appended claims as well as the scope of the appended claims.

The present disclosure relates to a device for determining whether to remove a Foley catheter. Specifically, the present disclosure relates to a device for determining whether to remove a Foley catheter from the bladder of a patient, into which the Foley catheter is inserted, due to a urination disorder or the like.

What is claimed is:

1. A device to be coupled to a Foley catheter already inserted into a bladder of a patient, the Foley catheter including a urine passage through which urine is discharged from the bladder, the device comprising:
   - a pressure sensor connected to a urine outlet of the urine passage and configured to measure a pressure value of the urine discharged through the urine outlet;
   - a connection tube disposed between the urine outlet and the pressure sensor and configured to have the urine discharged through the urine outlet and flow to the pressure sensor, wherein the connection tube is configured in a form in which a passage connected from the urine outlet branches off into a first branch and a second branch, the first branch is connected to the pressure sensor, and the second branch is formed so that a fluid is injected thereinto;
   - a check valve disposed in the second branch of the connection tube, wherein the check valve is configured so that the fluid passing through the second branch flows only toward the urine outlet;
   - a processor connected to the pressure sensor and configured to determine whether to remove the Foley catheter by comparing the pressure value with a predetermined threshold value, wherein the processor is configured to determine a start time of urine discharge as a time point at which the pressure value is greater than a predetermined specific value, determine an end time of the urine discharge as a time point at which the pressure value is smaller than the specific value, the specific value being smaller than the threshold value, and determine that the Foley catheter is to be removed when an average pressure value of the urine measured from the start time of the urine discharge to the end time of the urine discharge is greater than the threshold value, the specific value is a pressure value measured when the urine starts to be discharged in a state in which the Foley catheter and the device are inserted into a bladder of a normal person without a urination disorder, and the threshold value is a pressure value measured on average while the urine is discharged when the urine is normally discharged in a state in which the Foley catheter and the device are inserted into the bladder of the normal person without a urination disorder; and
   - a display unit connected to the processor and configured to display whether to remove the Foley catheter under control of the processor.

2. The device of claim 1, wherein the connection tube is configured so that the first branch is disposed on an extension line with the urine outlet, and the second branch is disposed obliquely with respect to the extension line of the urine outlet.

3. The device of claim 1, wherein the processor is further configured to determine that the Foley catheter is to be removed when the pressure value is maintained at a greater value than the threshold value for a predetermined time.

4. The device of claim 1, wherein the processor is further configured to determine that the Foley catheter is not to be removed when a peak value of the pressure value of the urine measured from the start point of the urine to the end time of the urine is smaller than the threshold value.

5. The device of claim 1, wherein the processor is further configured to determine that the Foley catheter is not to be removed when an average pressure value of the urine measured from the start time of the urine to the end time of the urine is smaller than the threshold value.

6. The device of claim 1, wherein the display unit includes a light emitting diode of at least one color and is configured so that a light emitting diode of a predetermined color corresponding to a removable state or a non-removable state of the Foley catheter among light emitting diodes of at least one color emits light under control of the processor.

* * * * *